United States Patent [19]

Lin et al.

[11] Patent Number: 5,055,611
[45] Date of Patent: Oct. 8, 1991

[54] PROCESS FOR RECYCLING AND REGENERATING CARBONYLATION CATALYST USED IN SYNTHESIS OF IBUPROFEN

[75] Inventors: Ronny W. Lin, Baton Rouge; R. Carl Herndon, Jr., Baton Rouge; E. E. Atkinson, Jr., Greenwell Springs, all of La.

[73] Assignee: Ethyl Corporation, Richmond, Va.

[21] Appl. No.: 621,815

[22] Filed: Dec. 4, 1990

[51] Int. Cl.$^5$ ............................................. C07C 51/10
[52] U.S. Cl. .................................................... 562/406
[58] Field of Search ........................ 560/105; 562/406

[56] References Cited

U.S. PATENT DOCUMENTS

| | | | |
|---|---|---|---|
| 4,013,583 | 3/1977 | Knifton | 562/522 |
| 4,013,584 | 3/1977 | Knifton | 562/522 |
| 4,038,208 | 7/1977 | Knifton | 560/233 |
| 4,042,530 | 8/1977 | Knifton | 560/233 |
| 4,048,093 | 9/1977 | Knifton | 562/406 |
| 4,981,995 | 1/1991 | Elango | 562/406 |

Primary Examiner—Michael L. Shippen
Attorney, Agent, or Firm—Richard J. Hammond

[57] ABSTRACT

A process for preparing ibuprofen is described. The improved process involves the treatment of spent palladium carbonylation catalyst with oxygen at about 300° C. to about 850° C. The treated material then used with a phosphine ligand to carbonylate 1-halo-1-(4-isobutylphenyl)ethane, 1-hydroxyl-1-(4-isobutylphenyl)ethane, or isobutylstyrene to produce ibuprofen.

10 Claims, No Drawings

PROCESS FOR RECYCLING AND REGENERATING CARBONYLATION CATALYST USED IN SYNTHESIS OF IBUPROFEN

This invention relates to a process for preparing a catalyst used in carbonylation processes. More particularly, this invention relates to a catalyst useful in the preparation of 2-(4-isobutylphenyl)propionic acid, a pharmaceutical commonly known as ibuprofen.

Among the prior art processes for the preparation of ibuprofen are those disclosed in European Patent Application 284,319 (Hoechst Celanese), which teaches that ibuprofen can be prepared by carbonylating 1-(4-isobutylphenyl)ethanol with carbon monoxide in an acidic aqueous medium and in the presence of a palladium phosphine complex and dissociated hydrogen and halide ions. These ions are preferably derived from a hydrogen halide. While this appears to be an attractive process, it has the disadvantage of starting with 1-(4-isobutylphenyl)ethanol, a compound which is not economical to make by presently known processes.

Co-pending application Ser. No. 07/395,017 (Knesel), filed Aug. 17, 1989, incorporated herein by reference, discloses a process for preparing 1-halo-1-(4-isobutylphenyl) ethane by reacting isobutylbenzene with hydrogen chloride or bromide and acetaldehyde at a temperature in the range of about $+10°$ C. to about $-35°$ C. in the presence of at least about 1.4 mols of hydrogen sulfate per mol of isobutylbenzene and in the absence of more than about 15% by weight of water, based on the weight of the hydrogen sulfate, the temperature being not higher than about $-10°$ C. when hydrogen chloride is employed. Knesel also teaches that his products can be carbonylated to form ibuprofen.

Co-pending application Ser. No. 07/270,621 (Stahly, et al.), filed Nov. 14, 1988, incorporated herein by reference, discloses a process for preparing 1-halo-1-(4-isobutylphenyl)ethane by reacting one molar proportion of isobutylbenzene with at least one molar proportion of alphachloroethyl ether or alpha-bromoethyl ether with agitation at a temperature in the range of about $0°$ C. to about $-35°$ C. in the presence of at least one molar proportion of hydrogen chloride or bromide and about 2-15 molar proportions of hydrogen sulfate. Like Knesel, Stahly, et al., teaches that their products can be carbonylated to form ibuprofen.

It has now been found that the prior art process of preparing ibuprofen by carbonylating a 1-halo-1-(4-isobutylphenyl)ethane or a 1-hydroxy-1-(4-isobutylphenyl)ethane or 4isobutylstyrene with carbon monoxide in an acidic aqueous medium at a temperature of at least about $10°$ C. and a carbon monoxide pressure of at least about 3.6 MPa in the presence of a complex of a palladium catalyst can be improved by treating a spent palladium carbonylation catalyst with oxygen at about $300°$ C. to about $850°$ C. and then mixing the treated catalyst with at least one stable, monodentate phosphine ligand.

According to the process of the present invention, the crude carbonylation product stream from the process of carbonylating a haloaromatic, hydroxyaromatic or styrenic compound is distilled or flashed under reduced pressure at the conclusion of the carbonylation reaction. The catalyst is concentrated in the bottom stream of the distillation vessel as the "heavy ends". These heavy ends may be recycled to catalyze a new batch carbonylation with or without a make-up of a fresh catalyst.

It is these "heavy ends" that represent the spent carbonylation catalyst useful in the process of the present invention. Such heavy ends (spent carbonylation catalyst) may be treated by the process of the present invention or a portion of such may be removed from the recycle stream and treated as described herein. As the result, it substantially reduces the consumption of the catalyst.

According to the process of the present invention, the "spent carbonylation catalyst" (obtained by one or more of the carbonylation processes noted above) is treated with oxygen at least about $300°$ C. to burn off tar and regenerate the catalyst for reuse. The oxygen may be economically obtained from air or pure oxygen may be used. When air is used, the treatment is carried out for a period of from about 60 minutes to about 48 hours, the shorter times usually generating acceptable treated catalyst when higher temperatures are used. However, temperatures in excess of $850°$ C. are to be avoided since unacceptable agglomeration of the catalyst particles occurs. Temperatures below $300°$ C. are less effective in regenerating the catalyst. Preferably, the temperature of treatment is from about $300°$ C. to about $850°$ C, most preferably from about $400°$ C. to about $600°$ C.

The spent carbonylation catalyst, treated as described above, is mixed with at least one acid-stable, monodentate phosphine ligand which is miscible with the organic phase of the carbonylation reaction. This complex may be added to the carbonylation reaction mixture as a preformed complex of palladium, such as a bis(triphenylphosphine)palladium compound, or it may be formed in situ by the separate addition to the reaction mixture of the monodentate phosphine ligand and the treated carbonylation catalyst. It is preferred, however, that the treated catalyst is further treated to form, for example, palladium compounds such as palladium (II) chloride, bromide, nitrate, sulfate, or acetate. Such further treatment is typically carried out with acid (hydrochloric, hydrobromic, etc.).

Phosphine ligands which may be used include trialkyl- and triarylphosphines such as tributyl-, tricyclohexyl-, and triphenylphosphine. Most preferred is triphenylphosphine.

The amount of regenerated palladium preferably employed is such as to provide from about 4 to 8,000 mols of 1-halo-1- (4-isobutylphenyl)ethane per mole of palladium; the most preferred amount provides about 200 to 2,000 mol of 1-halo-1-(4-isobutylphenyl)ethane per mol of palladium. The process is conducted in the presences of at least one mol of phosphine ligand per mol of palladium. Preferably about 2 to 40 mols of phosphorous ligand per mol of palladium are present in the carbonylation reaction, most preferably about 4 to about 20 mols of ligand per mol of metal.

As noted in the specification, compounds which are carbonylated in the practice of the invention comprise 1-halo-1-(4-isobutylphenyl)ethane, 1-hydroxy-1-(4-isobutylphenyl)ethane, and 4-isobutylstyrene.

The 1-halo-1-(4-isobutylphenyl)ethane used in one embodiment of this invention may be 1-chloro-1-(4-isobutylphenyl)ethane (CEBB) or 1-bromo-1-(4-isobutylphenyl)ethane, and it may be synthesized by any known technique. However, in preferred embodiments of the invention, the 1-halo-1-(4-isobutylphenyl)ethane is prepared by a process of Knesel, et al., cited earlier the teachings of which are incorporated herein in toto by reference. Methods of preparation of the 1-hydroxy-1-(4-isobutylphenyl)ethane are described in, for example, JP-106,403 issued Sept 5, 1986 or U.S. Pat. No. 4,843,172,172; and 4-isobutylstyrene preparations are described in, for example, U. S. Pat. No. 4,694,100 and U.S. Patent No. 4,329,507.

The 1-halo-1-(4-isobutylphenyl)ethane employed is a product that may be obtained by reacting one molar proportion of isobutylbenzene with at least one molar proportion of alphachloroethyl ether or alpha-bromoethyl ether with agitation at a temperature in the range of about 0° C. to about −35° C. in the presence of at least one molar proportion of hydrogen chloride or bromide and about 2-15 molar proportions of hydrogen sulfate. It is generally preferred to employ at least two molar proportions of the ether and about 2-6 molar proportions of the hydrogen sulfate per molar proportion of isobutylbenzene and to introduce the hydrogen chloride or bromide by bubbling it through the reaction mixture or by pressurizing the reaction vessel with it. The reaction is conducted in the absence of more than about 15% by weight of water, based on the weight of the hydrogen sulfate, in order to obtain a good yield of product with minimum co-formation of diarylethane by-product.

The 1-halo-1-(4-isobutylphenyl)ethane may also be obtained by reacting isobutylbenzene with hydrogen chloride or bromide and a stoichiometric deficit of acetaldehyde with agitation at a temperature in the range of about +10° C. to about −35° C. in the presence of an amount of sulfuric acid such as to provide at least two mols of hydrogen sulfate per mol of acetaldehyde and less than 1.5 mols of hydrogen sulfate per mol of isobutylbenzene, the temperature being not higher than about 10° C. when hydrogen chloride is employed. This process, which generally uses about 0.5-0.7 mol of acetaldehyde per mol of isobutylbenzene, has the advantage of not only minimizing the co-formation of diarylethane by-product but also avoiding the formation of the by-products that are formed from the acetaldehyde when it is used in larger amounts.

The carbonylation of the 1-halo-1-(4-isobutylphenyl)ethane, 1-hydroxy-1-(4-isobutylphenyl)ethane, or 4-isobutylstyrene substrate is conducted at a temperature of at least about 10° C., preferably about 50-130° C., and a carbon monoxide pressure of at least about 3.5 MPa, preferably about 4.8-10.5 MPa, in the presence of at least about one mol of water per mol of the 1-halo-1-(4-isobutylphenyl)ethane. An amount of water up to about 100 mols may be used, and an amount from about 8 to 14 mols of water per mol of the substrate is preferred. It is desirable for the reaction mixture to be acidified by the use of hydrochloric acid.

The presence of a solvent is not required in the process for the preparation of the treated catalyst, although it may be desirable in some circumstances. Those solvents which can be used include one or more of ketones, for example, acetone, methyl ethyl ketone, diethyl ketone, methyl propyl ketone, acetophenone, and the like; cyclic ethers, for example, tetrahydrofuran, dioxane, 1,3-dioxolane, and similar compounds; and aromatic hydrocarbons, for example, toluene, ethyl benzene, xylenes, and similar compounds. Acids and esters may also be used, such as acetic acid or ethyl acetate. Most highly preferred are ketones, especially methyl ethyl ketone (MEK).

The following examples are given to illustrate the process of this invention and are not intended as a limitation thereof.

EXAMPLES

General Preparation

The carbonylation was conducted in a 300 cc Hastelloy B autoclave equipped with a magnetically coupled agitator, a heating mantle, a temperature controller, a cooling coil, a vent line and a safety rupture disc. $PdCl_2$ (e.g. 0.05 milli gmole), $Ph_3P$ (0.5 milli gmole), alpha-chloroethyl-4-iso-butylbenzene (50 milli gmole or 9.82g), water (10 g) and MEK (25 g) were charged into the reactor under nitrogen atmosphere. (When "ash" was charged, the mixture added was its slurry in an aqueous HCl solution.) After purging the reactor with nitrogen, carbon monoxide was charged to the reactor through a dipleg to a desired carbon monoxide pressure (e.g., 1000 psig). With good agitation the reaction mixture was heated up to 125° C. and stirred for quantitative conversion (in 1-1.5 hours). Further additions of carbon monoxide were usually necessary during the carbonylation to maintain a proper pressure. After the reaction, the autoclave was cooled down and the excess carbon monoxide gas was vented. The carbonylation mixture was poured to a separate funnel and the ibuprofen organic solution was separated from the aqueous HCl solution.

The ibuprofen was stripped as the overhead product at about 1-3 mmHg absolute pressure from its solution (made in carbonylation runs without addition of MEK). The Pd catalyst was in the heel for reclamation by the process of the present invention. To reactivate the catalyst, the heel is charged in a crucible and oxidized by air in a furnace at about 300-450° C. until the tar was completely burned off (in about 2-4 hours). The resulting ash is then added to the reactor as described in the "General Preparation". The results are shown in Table I below.

TABLE I

| Example | % Chloroethyl-butylbenzene conversion | Ibuprofen yield % |
|---|---|---|
| 1 | 99.9 | 91.8 |
| 2 | 99.8 | 92.5 |
| Comparative 1* | 100.0 | 89.2 |
| Comparative 2* | 99.8 | 92.3 |

*Fresh unused catalyst is used in the carbonylation reaction.

General Recycle Preparation

For a further preparative technique as a general example of carrying out the recycle process of the present invention, the carbonylation mixture produced as indicated above is vacuum distilled to produce ibuprofen (and lighter ends) as a distillate faction. The distillation is carried out at about 1 to 3 mm Hg with the ibuprofen fraction coming over at about 100° to 170° C. (depending on the pressure). The distillation is halted when the distillate temperature exceeds 200° C. indicating undesirable heavier fractions. Upon cooling, the residue in the distilling vessel (mostly tars and catalyst) can be totally recycled for a further carbonylation or a portion can be withdrawn for regeneration in accordance with the present invention. Fresh catalyst is then added to the material for recycle as make-up.

The results of the recycle (and reuse of the catalyst before any regeneration) is shown in Table II.

TABLE II

| Example | % Chloroethyl-butylbenzene conversion | Ibuprofen yield % |
|---|---|---|
| 3* (Avg. of 2 runs) | 97.8 | 77.7 |
| Comparative** | 98.7 | 53.7 |

*Catalyst was recycled twice and no MEK was used for the carbonylation.
**Fresh catalyst was used without the use of MEK solvent.

We claim:

1. In a process for preparing ibuprofen which process comprises carbonylating a I-halo-1-(4-isobutylphenyl)ethane, 1-hydroxyl-1-(4-isobutylphenyl)ethane, or 4-isobutyl(styrene) with carbon monoxide in water or in an acidic aqueous medium at a temperature of at least about 10° C. and a carbon monoxide pressure of at least about 3.5 MPa in the presence of palladium catalyst, the improvement comprising forming said palladium catalyst by a process comprising:
  i) treating a spent palladium carbonylation catalyst with oxygen at about 300° C. to about 850° C.; and
  ii) mixing said treated carbonylation catalyst with a solution of at least one acid stable monodentate phosphine ligand.

2. A process of claim 1 where the treated palladium carbonylation catalyst is a palladium (II) compound.

3. A process of claim 2 wherein the palladium (II) compound is further treated to produce palladium (II) chloride.

4. A process of claim 2 wherein the palladium (II) compound is further treated to produce palladium (II) bromide.

5. A process of claim 1 wherein the ligand is a monodentate phosphine ligand.

6. A process of claim 1 wherein the ligand is a tri(hydrocarbyl)phosphine.

7. A process of claim 6 wherein the ligand is triphenylphosphine.

8. A process for preparing ibuprofen which comprises carbonylating 1-chloro-1-(4-isobutylphenyl)ethane with carbon monoxide in water or in an acidic medium containing methyl ethyl ketone as a solvent and about 8-24 mols of water per mol of 1-chloro-1-(4-isobutylphenyl)ethane at a temperature in the range of about 50-50° C. and a carbon monoxide pressure in the range of about 800-2000 psig in the presence of a carbonylation catalyst formed by a process comprising
  i) treating a spent carbonylation catalyst with oxygen at about 300° C. to about 850° C.; and
  ii) mixing said treated carbonylation catalyst with a solution of at least one acid stable, monodentate phosphine ligand.

9. A process of claim 8 wherein the treated carbonylation catalyst is a palladium (II) compound.

10. A process for recycling and regenerating a carbonylation catalyst used to prepare ibuprofen, the process comprising:
  i) distilling ibuprofen at reduced pressure from a carbonylation reaction mixture;
  ii) recycling the residue remaining from said distillation into a second carbonylation reaction;
  iii) removing a portion of said residue before said recycling and treating said removal portion with oxygen at about 300° C. to about 850° C. to from a regenerated catalyst;
  iv) adding the regenerated catalyst to carbonylation reaction mixture used to prepare ibuprofen.

* * * * *